United States Patent
Schröder

(10) Patent No.: US 6,516,653 B2
(45) Date of Patent: Feb. 11, 2003

(54) GAS SENSOR ARRANGEMENT

(75) Inventor: Willi Schröder, Dossau (DE)

(73) Assignee: MSA Auer GmbH, Berlin (DE)

( * ) Notice: Subject to any disclaimer, the term of this patent is extended or adjusted under 35 U.S.C. 154(b) by 0 days.

(21) Appl. No.: 09/829,132

(22) Filed: Apr. 9, 2001

(65) Prior Publication Data

US 2001/0052256 A1 Dec. 20, 2001

(51) Int. Cl.[7] .............................................. G01N 19/10
(52) U.S. Cl. ....................................................... 73/23.2
(58) Field of Search ........................... 73/23.2, 864.81, 73/863.83; 422/83; 96/111, 117

(56) References Cited

U.S. PATENT DOCUMENTS

| 5,054,328 A | * | 10/1991 | Long et al. | 73/864.81 |
|---|---|---|---|---|
| 5,286,943 A | * | 2/1994 | Has | 219/413 |
| 5,473,951 A | * | 12/1995 | Tomlin | 73/863.83 |
| 5,606,804 A | * | 3/1997 | Smith et al. | 34/261 |
| 5,624,639 A | * | 4/1997 | Ariga et al. | 422/83 |
| 5,685,895 A | * | 11/1997 | Hagiwara et al. | 96/117 |
| 5,861,053 A | * | 1/1999 | Noritake et al. | 96/111 |

FOREIGN PATENT DOCUMENTS

| DE | 3911767 | * | 10/1990 | C10L/10/00 |

* cited by examiner

*Primary Examiner*—Hezron Williams
*Assistant Examiner*—Jay L Politzer
(74) *Attorney, Agent, or Firm*—Wood, Phillips, Katz, Clark & Mortimer

(57) ABSTRACT

This invention relates to a gas sensor arrangement in which one or more gas sensors (4) are placed into rooms for monitoring or measuring gas or vapor concentrations or mixtures, a diffusion body (5) is placed in front of the gas sensors (4), the responsiveness of the gas sensors is impaired by structural design or contamination and/or the gas atmosphere is static. The sensor (4) or sensors (4.1 to 4.n) are placed in, on, or in front of a duct (1) located in the room and thus are within the flow area of said duct (1), and a flow is present in the duct (1) during measuring or monitoring. The duct can be artificially heated using a heater (6) to generate this flow.

12 Claims, 1 Drawing Sheet

GAS SENSOR ARRANGEMENT

BACKGROUND OF THE INVENTION

1. Field of the Invention

This invention is particularly suited for gas sensors with an upstream diffusion barrier whose responsiveness is impaired by structural design or contamination, or which are primarily used in static gas atmospheres.

2. Background Art

When gases or vapors reach the sensor(s) by diffusion through porous bodies, it is known that diffusion barriers with a diffusion gradient are formed that impair gas exchange, for gas diffusion through such barrier is determined by the partial pressure difference., Thus small measuring ranges and the required high responsiveness can no longer be achieved using conventional gas sensor arrangements, especially when diffusion barriers exist or in static gas atmospheres.

SUMMARY OF THE INVENTION

It is the problem of this invention to improve the dynamic properties of the gases and vapors under the conditions mentioned above. This problem is solved by the characterizing features of claim 1 while advantageous embodiments are the subject of the dependent claims. Claim 8 described an alternative use.

The gas sensor arrangement of the invention in which one or more gas sensors are configured to monitor or measure concentrations of gas, vapor or mixtures in rooms and in which the gas sensors are located behind an upstream diffusion barrier so that their responsiveness is impaired by structural design or contamination and/or the gas atmosphere is static, involves that the sensor(s) are located in, on and/or in front of a duct, i.e. in the flow area of this duct, and that a flow is present in this duct when the sensor(s) are measuring or monitoring. Most preferably, the duct extends from down upwards.

The flow can advantageously be generated by the natural difference in temperature, and/or the duct is artificially heated using a heater.

The invention utilizes the finding from practical measurements that even for small gas concentrations to be measured, signal change in remote measuring heads operating on the diffusion principle is clearly greater when the flow changes from near zero to low than when the flow changes from low to high.

In a preferred embodiment, the duct is a tube with at least one lateral opening, most simply a hole, through which the sensor has gas contact.

This module can easily be integrated in a casing that houses measuring and evaluation equipment. The upper and lower ends of the tube pass through the walls of the casing. The sensor may easily comprise an upstream diffusion body. In addition, this arrangement also allows for using dissipated energy from electronic or electric components inside the casing for heating the duct artificially.

DETAILED DESCRIPTION OF THE DRAWING

Figure 1:
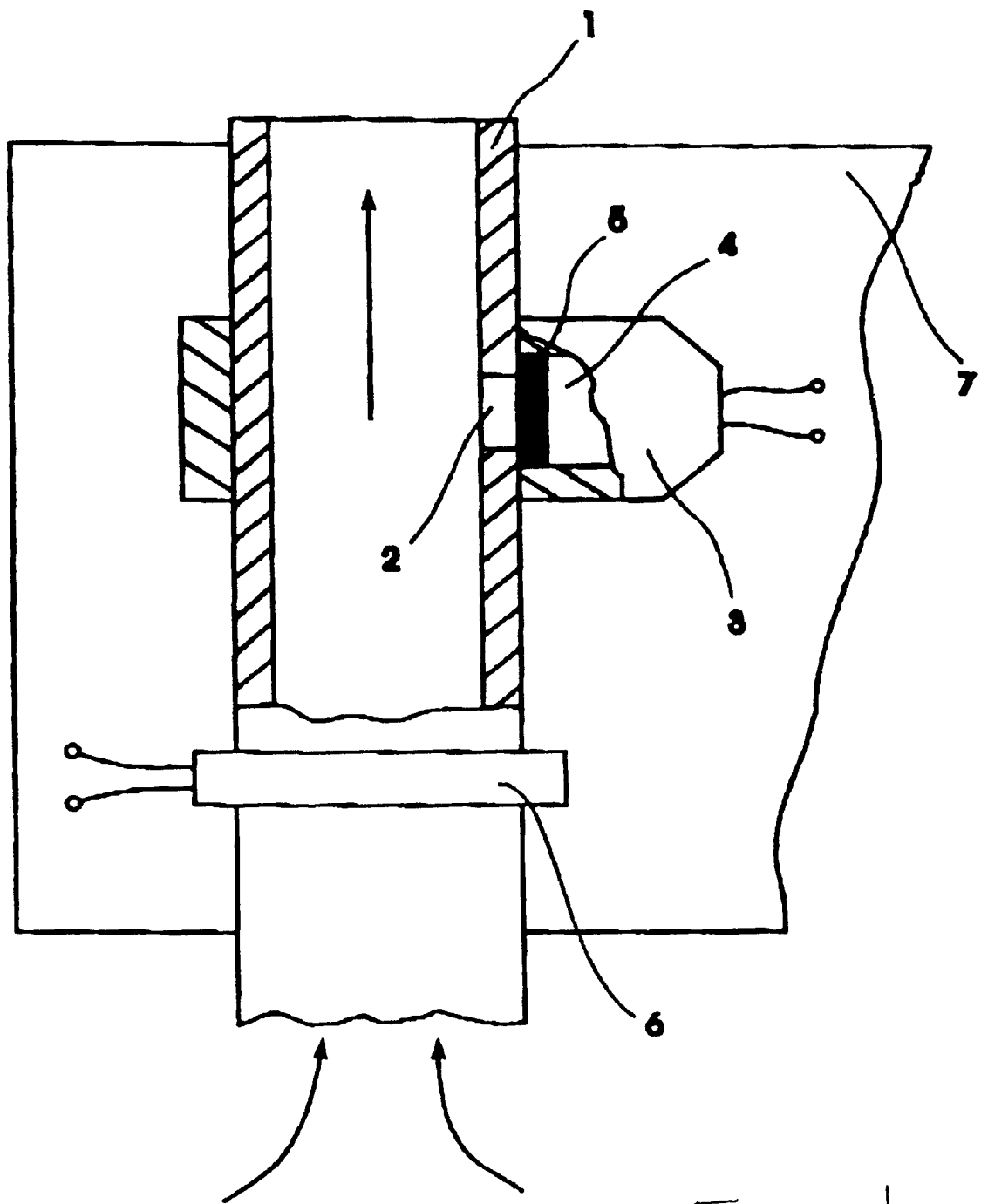
FIG. 1 is a partial cross-sectional view of a gas sensor arrangement, according to the invention.

An embodiment of a gas sensor arrangement, that is particularly suited for use as a conflagration gas detector in power stations, is described below with reference to the figure.

A duct 1 is tube-shaped and placed in a casing 7 in a space together with measuring and evaluation equipment, including a sensor arrangement 4, which may include, for example, at least one sensor for monitoring or measuring gas concentrations or mixtures. The at least one gas sensor may be placed in, on, or adjacent to the duct 1. The tube ends pass through the upper and lower casing walls so that gasses/vapors can flow through the tube without obstruction. In this embodiment, the duct 1 extends vertically, through this is not required. The tube has a wall with spaced end openings and a lateral opening 2 through the wall between the spaced end openings, which lateral opening is preferably a hole, through which the sensor arrangement 4 has gas contact. A diffusion body/filter 5, that has to be penetrated by the gas or vapor for measuring/monitoring, is placed in front of the sensor arrangement 4. The dissipated energy from electronic or electric components 8 in the casing 7 is used to artificially heat the tube used for the duct 1, which simultaneously cools the electronic or electric equipment 8. Heat may also be generated through a heater 6. At the same time, a constant flow is generated in the tube during measuring or monitoring that accelerates gas diffusion and gas/vapor exchange at the sensor arrangement 4. The responsiveness of the sensor arrangement 4 is considerably increased in this way without the requirement of an additional means to propel or force the gas/vapor through the duct 1.

The sensor arrangement, according to the invention, can also be transferred to measurements or monitoring in water where responsiveness is changed by bubbles that form on water electrodes. This arrangement would have an immersion tube instead of the duct 1 and, for example, a water electrode instead of the gas sensor 4. When a constant flow is induced in the immersion tube, for example, by artificial heating, bubble deposition on the water electrode that is in the flow area of the immersion tube is prevented or reduced, thus considerably increasing responsiveness.

The inventive system is usable to induce flow to the sensor arrangement 4 that is otherwise impaired by a) structural design, b) static conditions in the space, and/or c) blockage of the diffusion body/filter 5.

The duct 1 is tube-shaped and placed in a casing 7 together with measuring and evaluation equipment. The tube ends pass through the upper and lower casing walls so that gases and vapors can flow through the tube without obstruction. The tube comprises a lateral opening 2, preferably a hole, through which the sensor has gas contact. A diffusion body 5 that has to be penetrated by the gas or vapor for measuring/monitoring is placed in front of the sensor 4. The dissipated energy from electronic or electric components 8 in the casing 7 is used to artificially heat the tube used as duct 1 with the heater 6, which simultaneously cools the electronic or electric equipment. At the same time, a constant flow is generated in the tube during measuring or monitoring that accelerates gas diffusion and gas or vapor exchange at the sensor 4. The responsiveness of sensor 4 is considerably increased in this way.

The sensor arrangement according to the invention can also be transferred to measurements or monitoring in water where responsiveness is changed by bubbles that form on water electrodes. This arrangement would comprise an immersion tube instead of the duct and, for example, a water electrode instead of the gas sensor. When a constant flow is generated in the immersion tube, for example, by artificial heating, bubble deposition on the water electrode that is in the flow area of the immersion tube is prevented or reduced, thus considerably increasing responsiveness.

I claim:

1. In combination:

(a) a space having a gas therein;

(b) a duct in the space which induces convention movement of the gas within the duct; and (c) a sensor arrangement comprising: (i) at least one gas sensor in the space for monitoring or measuring gas concentrations or mixtures; and (ii) a diffusion barrier/filter in front of the at least one gas sensor, the responsiveness of the at least one gas sensor being at least one of a. impaired by structural design or blockage of the diffusion body/filter or b. impaired by reason of the gas being static within the space, wherein the at least one gas sensor is placed in, on, or adjacent to the duct located in the space and thus within a flow area of said duct such that a flow of the gas is induced by the duct during measuring or monitoring without requiring any additional means to propel gas in the duct.

2. The combination according to claim 1, characterized in that the duct extends vertically.

3. The combination according to claim 1, characterized in that the duct is artificially heated using a heater to induce convective movement of the gas.

4. The combination according to claim 1, characterized in that the duct is designed as a tube with a wall having spaced end openings and at least one lateral opening through the wall between the spaced end openings through which the at least one gas sensor has gas contact.

5. The combination according to claim 1, characterized in that the duct passes through a casing that houses measuring and evaluation equipment including the at least one gas sensor, and has spaced top and bottom end openings and the at least one gas sensor is connected to the inside of the duct via an opening between the top and bottom end openings.

6. The combination according to claim 4 or 5, characterized in that a diffusion body/filter that has to be penetrated by the gas for measurement or monitoring is placed in front of the at least one gas sensor.

7. A gas sensor arrangement in which at least one gas sensor is placed into a space for monitoring or measuring gas concentrations or mixtures, a diffusion barrier/filter is placed in front of the at least one gas sensor, the responsiveness of the at least one gas sensor is impaired by structural design or blockage of the diffusion barrier/filter and/or the gas in the space is static, wherein the at least one gas sensor is placed in, on, or adjacent to a duct located in the space so as to be within a flow area of said duct, so that a flow is present in the duct during measuring or monitoring, wherein the duct passes through a casing and is artificially heated using at least one of a) a heater and b) dissipated energy from electronic or electric equipment inside the casing to induce gas flow in the duct without requiring any additional means to propel gas in the duct.

8. A gas sensor arrangement in which at least one gas sensor is placed into a space for monitoring or measuring gas concentrations or mixtures, a diffusion barrier/filter is placed in front of the at least one gas sensor, the responsiveness of the at least one gas sensor is impaired by at least one of structural design or blockage of the diffusion barrier/filter and/or the gas atmosphere in the space is static, wherein the at least one gas sensor is placed in, on, or adjacent to a duct located in the space so as to be within a flow area of said duct, wherein a flow is present in the duct during measuring or monitoring, wherein the duct passes through a casing, wherein a diffusion body/filter that has to be penetrated by the gas for measurement or monitoring is placed in front of the at least one gas sensor, wherein the dissipated energy from electronic or electric equipment inside the casing is used for artificially heating the duct and inducing gas flow in the duct without requiring any additional means to propel gas in the duct.

9. A gas sensor arrangement in which at least one gas sensor is placed into a space for monitoring or measuring gas concentrations or mixtures, a diffusion barrier/filter is placed in front of the at least one gas sensor, the responsiveness of the at least one gas sensor is impaired by at least one of structural design or blockage of the diffusion barrier/filter and/or the gas in the space is static, wherein the at least one gas sensor is placed in, on, or adjacent a duct located in the space so as to be within a flow area of said duct, wherein a flow is present in the duct during measuring or monitoring, wherein the duct passes through a casing that houses measuring and evaluation equipment and has a wall with open, spaced bottom and top ends, and the at least one gas sensor is connected to the inside of the duct via an opening through the wall between the bottom and top ends, wherein a diffusion body/filter that has to be penetrated by the gas for measurement or monitoring is placed in front of the at least one gas sensor, wherein dissipated energy from electronic or electric equipment inside the casing is used for artificially heating the duct and inducing gas flow in the duct without requiring any additional means to propel gas in the duct.

10. The gas sensor arrangement according to claim 8, wherein the duct extends vertically.

11. The sensor arrangement according to claim 8, characterized in that the duct is artificially heated using a heater.

12. The gas sensor arrangement according to claim 8, wherein the duct is designed as a tube with a wall and at least one lateral opening through the wall and comprising a hole, through which the at least one sensor has gas contact.

* * * * *